(12) United States Patent
Wang

(10) Patent No.: US 10,290,100 B2
(45) Date of Patent: May 14, 2019

(54) METHOD FOR IMPLEMENTING CONTROL OF DISPLAY OF HIGHLIGHTED AREA ON DISPLAY

(71) Applicant: NANJING JUSHA DISPLAY TECHNOLOGY CO., LTD., Nanjing (CN)

(72) Inventor: Wei Wang, Nanjing (CN)

(73) Assignee: Nanjing Jusha Display Technology Co., Ltd., Jiangsu Province (CN)

( * ) Notice: Subject to any disclaimer, the term of this patent is extended or adjusted under 35 U.S.C. 154(b) by 0 days.

(21) Appl. No.: 15/568,877

(22) PCT Filed: May 21, 2015

(86) PCT No.: PCT/CN2015/079435
§ 371 (c)(1),
(2) Date: Oct. 24, 2017

(87) PCT Pub. No.: WO2016/173013
PCT Pub. Date: Nov. 3, 2016

(65) Prior Publication Data
US 2018/0108127 A1    Apr. 19, 2018

(30) Foreign Application Priority Data

Apr. 28, 2015    (CN) .......................... 2015 1 0206020

(51) Int. Cl.
*A61B 6/00*       (2006.01)
*G06T 7/00*       (2017.01)
(Continued)

(52) U.S. Cl.
CPC ............ *G06T 7/0012* (2013.01); *A61B 6/469* (2013.01); *G06F 19/00* (2013.01); *G06T 7/11* (2017.01);
(Continued)

(58) Field of Classification Search
None
See application file for complete search history.

(56) References Cited

U.S. PATENT DOCUMENTS 5,644,739 A * 7/1997 Moursund ............... G06F 9/451
                                                             715/840
5,777,616 A * 7/1998 Bates ...................... G06F 3/0486
                                                             715/837
(Continued)

FOREIGN PATENT DOCUMENTS

CN        1447232 A      10/2003
CN        1858842 A      11/2006
(Continued)

OTHER PUBLICATIONS

International Search Report dated Jan. 26, 2016, directed to International Application No. PCT/CN2015/079435; 6 pages.

*Primary Examiner* — Nancy Bitar

(57) ABSTRACT

This invention discloses a method to control highlighting of certain part of image on a display, wherein the image processing unit forwards the physical coordinates acquired by the host computer's coordinate acquisition unit to the coordinate transmission unit, and draws a regular shape centered on the acquired physical coordinates, and then displays the area within the regular shape at the normal brightness, and the rest outside the area at the corresponding proportion of low brightness. According to the method of the present invention, the attention of the doctor is focused on the specific or targeted area, the interferences caused by the surrounding images and the brightness are shielded, and the images in the specific pattern area is easier to identify. Thus, it will help doctors to improve the efficiency and accuracy of medical diagnosis for a lesion and make medical consultation and education more convenient.

6 Claims, 2 Drawing Sheets

(51) Int. Cl.
  *G16H 30/40* (2018.01)
  *G06F 19/00* (2018.01)
  *G06T 7/11* (2017.01)

(52) U.S. Cl.
  CPC ... *G16H 30/40* (2018.01); *G06T 2207/10072* (2013.01); *G06T 2207/30004* (2013.01)

(56) References Cited

U.S. PATENT DOCUMENTS

| | | |
|---|---|---|
| 8,373,728 B2 | 2/2013 | Ozawa et al. |
| 2003/0179238 A1 | 9/2003 | Roh |
| 2007/0146344 A1* | 6/2007 | Martin .................. G06F 1/3215 345/173 |
| 2010/0182332 A1* | 7/2010 | Ozawa .................. G06F 1/3203 345/589 |
| 2014/0298276 A1* | 10/2014 | Yokoyama ............ G06F 1/3265 715/863 |
| 2014/0327692 A1 | 11/2014 | Mishra et al. |

FOREIGN PATENT DOCUMENTS

| | | |
|---|---|---|
| CN | 101432796 A | 5/2009 |
| EP | 2763022 A1 | 8/2014 |

* cited by examiner

METHOD FOR IMPLEMENTING CONTROL OF DISPLAY OF HIGHLIGHTED AREA ON DISPLAY

FIELD OF THE INVENTION

This invention relates to a method to control highlighting of certain part of image on a display.

BACKGROUND OF THE INVENTION

With the continuous development of science, technology and healthcare industry, doctor's requirement for high performance of displaying medical image is increasing so as to improve efficiency and accuracy of medical diagnosis, and the displays intended for medical use are used more and more in hospitals and medical institutions. Compared with conventional displays, the displays for medical use are higher in brightness and resolution and also characterized by professional curves for special needs. Conventional professional medical displays have the same brightness in full-screen so that a doctor's attention can not be better focused on a specific lesion, and susceptible to the surrounding image and brightness interference. A method to control highlighting of certain part of image in a display enables the areas other than the specific graphics area to be displayed in low brightness, so that the eyes of the doctor are focused on the specific area, the interference caused by the surrounding image and the brightness is shielded, and the images in the specific pattern area is easier to identify. Thus, it will help doctors to improve the efficiency and accuracy of medical diagnosis for a lesion and make consultation and medical education more convenient.

SUMMARY OF THE INVENTION

This invention is to provide a method to control highlighting of certain part of image on a display, by which the attention of the doctor is focused on the specific part, the interferences caused by the surrounding images and the brightness are shielded, and the images in the specific part is easier to identify. Thus, it will help doctors to improve the efficiency and accuracy of medical diagnosis for a lesion and make medical consultation and education more convenient.

In order to achieve the above-said purpose, according to a first embodiment, provided is a method to control highlighting of certain part of image on a display, which includes a host computer's coordinate acquisition unit (or referred to as application software's coordinate acquisition unit), a coordinate transmission unit, an image processing unit, an instant triggering unit (or referred to as one-key triggering unit), a host computer software interface hidden unit (or referred to as interface of application software hidden unit).

Further, a certain shape of part or area on the entire display screen is displayed at the normal brightness, and the other parts or areas are displayed at the corresponding proportion of low brightness.

Further, said shape may be circular, oval, square, or irregular shaped, and its area may be a variety of adjustable areas smaller than the screen area.

Further, the above-said corresponding proportion is a variety of adjustable ratios of less than 100%.

Further, the host computer's coordinate acquisition unit captures the origin coordinates and the cursor position coordinates of the display, and the difference between the two sets of the coordinates is the physical coordinates of the cursor position relative to the display, i.e., the relative coordinates.

Further, the host computer forwards the acquired physical coordinates of the cursor position relative to the display to the coordinate transmission unit through the related protocol, and the coordinate transmission unit forwards the coordinates to the image processing unit through the related protocol.

Further, the image processing unit firstly draws a rectangle centered on the acquired coordinates, the coordinates of the upper left corner and the lower right corner of the rectangle using as the starting point and the end point of the area respectively, and then draws the desired pattern within the rectangle, determines the boundary point coordinates of the specific pattern, and distinguishes the specific pattern area from other areas;

the image processing unit marks the area within the specific pattern boundary point as 1, and the other areas outside the specific pattern boundary point as 0, and stores the information in the corresponding register, and then conducts addressing and scanning about all the pixels of the display in order, and addressing is started when the rectangular area is scanned;

the original R, B values remain unchanged when the addressed coordinates are marked as 1;

the R, G and B values are reduced according to the corresponding proportion on the original basis when the addressed coordinates are marked as 0; and the R, G and B values of the other areas outside the rectangle are reduced according to the corresponding proportion on the original basis, thereby achieve the different brightness display of the specific pattern area from other areas.

When the coordinate transmission unit senses the triggering of the related key and informs the host computer through the related protocol, the host computer controls the entry or exit of area display mode according to the received instruction, wherein the area display mode is turned off by default in the default state, and the area display mode is turned on when the related key is triggered for the first time, and the area display mode is turned off when the related key is triggered again.

The host computer software will start automatically when the computer is turned on and the software's interface is hidden.

According to a second embodiment, provided is a method to control highlighting of certain part of image on a display, which comprises a host computer's coordinate acquisition unit (or application software's coordinate acquisition unit), a coordinate transmission unit, and an image processing unit, wherein the image processing unit forwards the physical coordinates acquired by the host computer's coordinate acquisition unit to the coordinate transmission unit, and draws a regular shape centered on the acquired physical coordinates, and then displays the area within the regular shape at the normal brightness, and the rest outside the area at the corresponding proportion of low brightness.

Advantages of the present invention include:

According to the method of the present invention, the attention of the doctor can be attracted to the specific or targeted area, the interferences caused by the surrounding images and the brightness can be shielded, and the images in the specific area will be easier to identify. Thus, it will help doctors to improve the efficiency and accuracy of medical diagnosis for a lesion and make medical consultation and education more convenient.

BRIEF DESCRIPTION OF THE DRAWINGS

The following part further explains the invention with descriptions of drawings and application case.

BEST MODE FOR CARRYING OUT THE INVENTION

Figure 1:
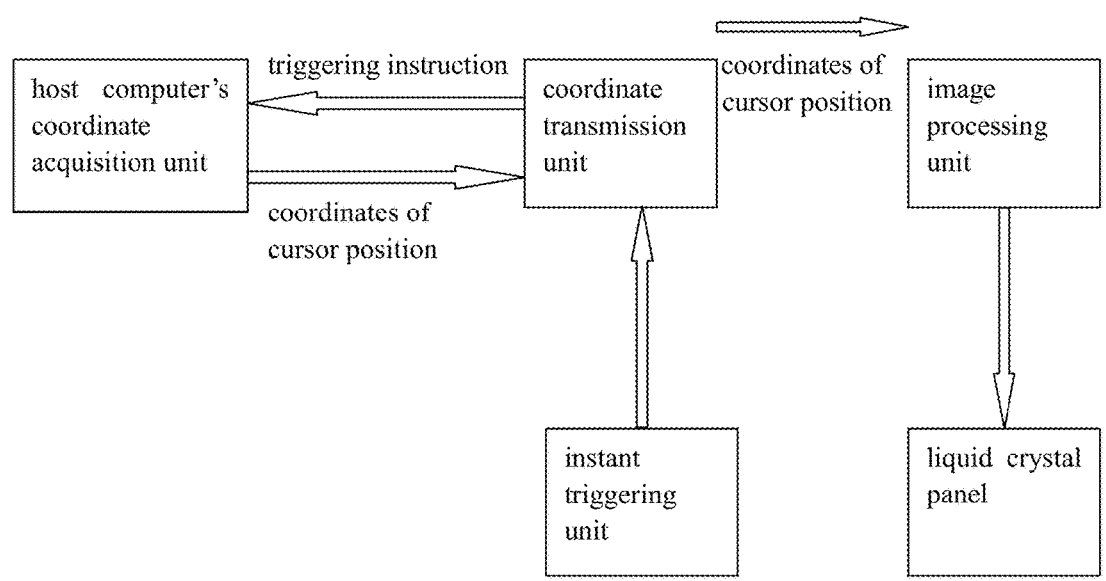
FIG. 1 is a structural frame diagram of the present invention.
Figure 2:
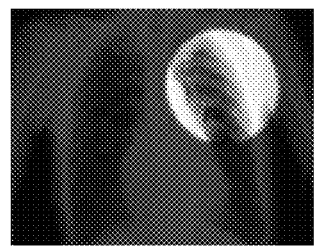
FIG. 2 is a view showing the application effect of the present invention.

Example: FIG. 1-2 shows an example of a method to control highlighting of certain part of image on a display, which uses the hardware including a host computer, an image processing unit connected to the host computer, and a display panel connected to the image processing unit, and the display panel is preferably a liquid crystal panel. The host computer comprises an instant triggering unit, a coordinate transmission unit, a host computer software interface hidden unit (or interface of application software hidden unit) and a host computer's coordinate acquisition unit (or application software's coordinate acquisition unit). The instant triggering unit triggers the related key, the coordinate transmission unit recognizes the triggering action and sends the triggering action to the host computer through the related protocol as a certain triggering instruction. The host computer receives the triggering instruction and conducts acquisition and conversion of the coordinates of the cursor position through host computer's coordinate acquisition unit, and further forwards the finally acquired physical coordinates of cursor position relative to the display to the coordinate transmission unit through the related protocol. The coordinate transmission unit forwards the coordinates to the image processing unit through the related protocol. The image processing unit draws a corresponding size of pattern centered on the received coordinates, distinguishes the specific pattern area from other areas, and the R, G and B values of other areas outside the specific pattern area are reduced according to the corresponding proportion on the original basis and the R, B values of the specific pattern area remain unchanged, thereby achieve the different brightness display of the specific pattern area from other areas and highlight the image within the specific pattern area. The related protocol shall comply with the corresponding serial port mechanism and ensure the accuracy of data transmission, and is generally composed of beginning flag (header), data length, data bits and parity bits (or check bits). The calculation of the relative coordinates is especially applicable to the case where a host computer is connected to multiple displays. At this point, the top left coordinates (origin coordinates) of the other displays other than the main display are not (0,0). Before calculating the relative coordinates, the captured upper left corner coordinates (origin coordinates) of the respective displays will be sorted, and then the coordinates of the cursor position and the coordinates of the upper left corner of the respective displays (origin coordinates) are compared to determine which display the cursor is on. Hereafter, the difference of the coordinates of the cursor position and those of the corresponding upper left corner coordinates (origin coordinates) are obtained to calculate relative coordinates. The host computer software will start automatically when the computer is turned on and the software's interface is hidden, which does not affect the user's normal operation of the displays.

The invention can realize the different brightness display of the specific graphics area from other areas. The cursor position acquisition is realized by the host computer, and the related brightness control is carried out by the image processing technology. The specific pattern can be regular or irregular shapes such as round, oval, square and the like. The brightness ratio of the specific pattern to the other area can be changed as required.

It is to be understood that the above-described example is merely illustrative of the technical concept and features of the present invention and are intended to enable those skilled in the art to understand the solution of the invention and to practice without limiting the scope of the invention. Any equivalent alterations or modifications made based on the spirit of the essential technical solutions of the present invention shall be covered by the scope of the present invention.

The invention claimed is:

1. A method to control highlighting of certain part of image on a display, characterized by it includes a host computer's coordinate acquisition unit, a coordinate transmission unit, an image processing unit, an instant triggering unit, a host computer software interface hidden unit;

the host computer's coordinate acquisition unit captures the origin coordinates and the cursor position coordinates of the display, and the difference between the two sets of the coordinates is the physical coordinates of the cursor position relative to the display;

the host computer forwards the acquired physical coordinates of the cursor position relative to the display to the coordinate transmission unit through the related protocol, and the coordinate transmission unit forwards the coordinates to the image processing unit through the related protocol;

the image processing unit firstly draws a rectangle centered on the acquired coordinates, the coordinates of the upper left corner and the lower right corner of the rectangle using as the starting point and the end point of the area respectively, and then draws the desired pattern within the rectangle, determines the boundary point coordinates of the specific pattern, and distinguishes the specific pattern area from other areas;

the image processing unit marks the area within the specific pattern boundary point as 1, and the other areas outside the specific pattern boundary point in the rectangle as 0, and stores the information in the corresponding register, and then conducts addressing and scanning about all the pixels of the display in order, and addressing is started when the rectangular area is scanned;

the original R, G, B values remain unchanged when the addressed coordinates are marked as 1;

the R, G and B values are reduced according to the corresponding proportion on the original basis when the addressed coordinates are marked as 0; and the R, G and B values of the other areas outside the rectangle are reduced according to the corresponding proportion on the original basis, thereby achieve the different brightness display of the specific pattern area from other areas.

2. The method according to claim 1, characterized by a certain shape of area on the entire display screen is displayed at the normal brightness, and the other areas are displayed at the corresponding proportion of low brightness.

3. The method according to claim 2, wherein said shape is circular, oval, square, or irregular shaped, and its area is a variety of adjustable areas smaller than the screen area.

4. The method according to claim 2, wherein the corresponding proportion of low brightness is a variety of adjustable ratios of less than 100%.

5. The method according to claim 1, wherein when the coordinate transmission unit senses the triggering of the relevant key and informs the host computer through the related protocol, the host computer controls the entry or exit of area display mode according to the received instruction, the area display mode is turned off by default in the default state, and the area display mode is turned on when the related key is triggered for the first time, and the area display mode is turned off when the relevant key is triggered again.

6. The method according to claim 1, wherein the host computer software will start automatically when the computer is turned on and the software's interface is hidden.

* * * * *